US007329258B2

(12) United States Patent
Studer

(10) Patent No.: US 7,329,258 B2
(45) Date of Patent: *Feb. 12, 2008

(54) DAMPING ELEMENT

(75) Inventor: Armin Studer, Winterthur (CH)

(73) Assignee: Synthes (U.S.A.), West Chester, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/497,875

(22) PCT Filed: Dec. 7, 2001

(86) PCT No.: PCT/CH01/00705

§ 371 (c)(1), (2), (4) Date: Nov. 4, 2004

(87) PCT Pub. No.: WO03/047441

PCT Pub. Date: Jun. 12, 2003

(65) Prior Publication Data

US 2005/0065514 A1 Mar. 24, 2005

(51) Int. Cl.
*A61B 17/56* (2006.01)
*A61F 2/30* (2006.01)

(52) U.S. Cl. .......................................................... 606/61

(58) Field of Classification Search .................. 606/60, 606/61; 267/80, 81, 83, 84, 86, 91, 93
See application file for complete search history.

(56) References Cited

U.S. PATENT DOCUMENTS 3,559,976 A * 2/1971 Jerz, Jr. ...................... 267/290
3,862,751 A * 1/1975 Schwaller .................... 267/91

(Continued)

FOREIGN PATENT DOCUMENTS

DE 1 127 671 4/1962

(Continued)

OTHER PUBLICATIONS

WO 99/40866, Interspinouts Stabiliser to be Fixed to Spinous Processes of Two Vertebrae, Publication Date: Aug. 19, 1999.

*Primary Examiner*—Anuradha Ramana
(74) *Attorney, Agent, or Firm*—Stroock & Stroock & Lavan LLP

(57) ABSTRACT

A damping element (1) comprising (a) two spring elements (2, 4) which are coaxial with or parallel to a longitudinal axis (3) and two axially end-wise connectors (5, 6) which can be linked to the spring elements (2, 4), where (b) the first spring element (2) exhibits a spring rate F, (c) the second spring element (4) exhibits a spring rate f, and (d) the spring rates F and f are different. A system stabilizing adjacent vertebras includes: (a) N pedicle screws or pedicle hooks (12), with N≧3, and (b) at least one pedicle screw or one pedicle hook having a receiving device (13) which simultaneously allow receiving two parallel affixation devices (7), and where (c) an element (14) acting as a spring is used for affixation between the minimum of one pedicle screw or pedicle hook (12) including a receiving device (13) and a further adjacent pedicle screw or pedicle hook (12).

28 Claims, 3 Drawing Sheets

U.S. PATENT DOCUMENTS

| | | | | | |
|---|---|---|---|---|---|
| 3,977,397 | A | * | 8/1976 | Kalnberz et al. | 606/57 |
| 4,516,955 | A | * | 5/1985 | Worner et al. | 464/89 |
| 5,306,310 | A | * | 4/1994 | Siebels | 623/17.13 |
| 5,423,816 | A | * | 6/1995 | Lin | 606/61 |
| 5,540,688 | A | | 7/1996 | Navas | |
| 5,639,278 | A | * | 6/1997 | Dereume et al. | 623/1.13 |
| 5,672,175 | A | * | 9/1997 | Martin | 606/61 |
| 5,733,284 | A | * | 3/1998 | Martin | 606/61 |
| 5,895,032 | A | * | 4/1999 | Simuttis | 267/140.12 |
| 6,136,031 | A | * | 10/2000 | Middleton | 623/17.16 |
| 6,402,750 | B1 | * | 6/2002 | Atkinson et al. | 606/61 |

FOREIGN PATENT DOCUMENTS

| | | | | |
|---|---|---|---|---|
| DE | 4109941 | A1 | * | 10/1992 |
| FR | 2717370 | A1 | * | 9/1995 |
| GB | 979433 | A | | 1/1965 |
| SU | 313 538 | A | | 10/1974 |

* cited by examiner

DAMPING ELEMENT

CROSS REFERENCE TO RELATED APPLICATION

This is a national stage of PCT International Application No. PCT/CH01/00705, filed Dec. 7, 2001.

FIELD OF THE INVENTION

The present invention relates to a damping element as defined in the preamble of claim 1 and to a system stabilizing adjacent vertebras as defined in the preamble of claim 15.

BACKGROUND OF THE INVENTION

The French patent document FR-A-2,799,949 discloses a spinal fixing system consisting of a number of tulip-like pedicle screws which in lieu of the conventional rigid longitudinal support are connected to each other by spiral spring elements. While the length of the spiral springs is adjustable, this design only allows a change in the spring force between two adjacent pedicle screws and hence between two adjacent vertebras. This document allows no conclusion whether the spring elements are mounted prestressed between the pedicle screws.

Another spinal fixation system is known from the European patent document EP-A-0,516,567, said system consisting of a number of tulip-like pedicle screws which are connected to each other by single damping elements instead of the conventional rigid longitudinal support. This system entails the drawback that only compressive forces between the pedicle screws may be absorbed. The damping elements moreover being of a fixed length, the design of this document provides a substantial number of such damping elements of different lengths in order to allow affixing a damping element of appropriate length between two implanted pedicle screws. Such a design is awkward and entails storing a significant number of damping elements of different lengths.

Another spinal fixation system is known from the European patent document EP-B-0,669,109 which consists of a number of pedicle screws with pierced heads, said screws being connected to each other not by the conventional longitudinal rigid support but by an elastic plastic band that can be pulled through the boreholes in the pedicle screws. Hollow-cylindrical bracing elements that may absorb any compressive forces between pedicle screws are arrayed on the plastic band between the individual pedicle screws. This system incurs many drawbacks.

In the first place the plastic band and the bracing elements must be threaded into or between the boreholes of the pedicle screws which already have been implanted, entailing complexity and loss of time for the surgeon. In the second place the somewhat elastic band is not prestressed. Because the supporting body length is fixed in this system too, nominal rupture sites at the support body are proposed to allow the surgeon to cut said body to size during the surgery. This is a complex and time-consuming procedure for the surgeon and might in general result in too short a bracing element, as a result of which its damping would be effective only after a given delay—this circumstance manifestly being undesirable.

SUMMARY OF THE INVENTION

The objective of the present invention is palliation of the above drawbacks. The invention aims to create a combined, prestressed tensile-compressive element which is affixable between two pedicle screws or pedicle hooks and which on one hand acts as a tensile spring element of a given spring rate and on the other hand as a compressive element having another spring rate.

The present invention solves this problem by a damping element exhibiting the features of claim 1 and by a system stabilizing adjacent vertebras which exhibits the features of claim 15.

In the preferred embodiment of the damping element of the invention, one of the spring elements is mounted as a compression spring. When the damping element has been installed, the connectors configured at the ends of the spring elements touch the ends of the compression spring element, as a result of which the first spring element may be tensively loaded and be prestressed.

Essentially the advantages offers by the present invention are as follows:

- unitary tensile/compressive element of which the length is adjustable,
- the damping properties may be varied by selecting inner cylinders of different lengths,
- the prestressing force present in the aforementioned state of the damping element is clearly defined and may be selected by the surgeon to match the different patient weights and the different surgical indications,
- after traction has been applied to the vertebras, the damping elements may be inserted in quick and simple manner between the pedicle screws and then be affixed to them.

In one embodiment of the damping element of the invention, the spring elements are designed to exhibit a constant spring rate. As a result, the unloaded spring elements' states may be restored after the damping element has been relieved.

In another embodiment of the damping element of the invention, its cross-section orthogonal to the longitudinal axis is reniform. Such a design offers the advantages that when implanting one or several damping elements, for instance in the process of spinal column fixation, said elements may be positioned more advantageously with respect to vertebral extensions or other implant components.

Further advantageous embodiments of the present invention are characterized in the dependent claims.

The system of the invention stabilizing adjacent vertebras essentially comprises several pedicle screws or pedicle hooks which may be linked to different affixation means. The affixation means between two pedicle screws or pedicle hooks illustratively may be bar-shaped longitudinal supports, springs or damping elements of the present invention.

At least one pedicle screw or one pedicle hook comprises receiving means allowing simultaneously receiving two parallel, longitudinal affixation means. In this manner an element acting as a spring, for instance a damping element of the invention, may be used for affixation between at least pedicle screw or pedicle hook fitted with receiving means and a further adjacent pedicle screw or pedicle hook.

Pedicle screws or pedicle hooks that are fitted with receiving means allowing concurrent connection between two parallel, longitudinal affixation elements and the pedicle screw or pedicle hook are known for instance from U.S. Pat. No. 4,653,481 (Howland). Similarly to the longitudinal supports cited in said patent, the damping elements of the present invention may be affixed by means of bars mounted on the connectors parallel to the longitudinal axis for instance in parallel ducts to the screw heads. Very easily and without further manipulation, the damping element displaceability in the ducts parallel to the longitudinal axis allows inserting a damping element of the present invention—which was prestressed to a desired spring force before implantation—into the receiving means at the pedicle screws. The compensation in length at different spacings between the pedicle screws or pedicle hooks is implemented by the axial displaceability of the bar-shaped connectors which are configured end-wise parallel to the longitudinal axis and which are situated at the damping elements of the invention in the ducts that are also parallel to the longitudinal axis.

Illustratively prestressing the damping element allows taking into account a number of instabilities, indications or patient weight. In the case of extension of the pertinent spinal segments, the damping element is compressed, whereas in the case of flexion of the pertinent spinal segment it is tensioned. The selections of the spring material, for instance a polymer, preferably a polycarbonate urethane (PCU) for the compressively loaded spring, and of metal for the tensively loaded spring element, of the geometric dimensions as well as the prestressing of the tensively loaded spring element allow optimally matching the system of the present invention to a patient's biomechanical particulars.

Essentially the advantages of the system of the present invention are as follows:

harmonic transition in rigidity from the stabilized spinal segment to the healthy spinal segments, the damping elements may be combined selectively in segments with rigid bars.

BRIEF DESCRIPTION OF THE DRAWINGS

The invention and further design modes of it are elucidated below in relation to several illustrative modes of implementation shown in partly schematic manner.

DETAILED DESCRIPTION OF THE INVENTION

Figure 1:
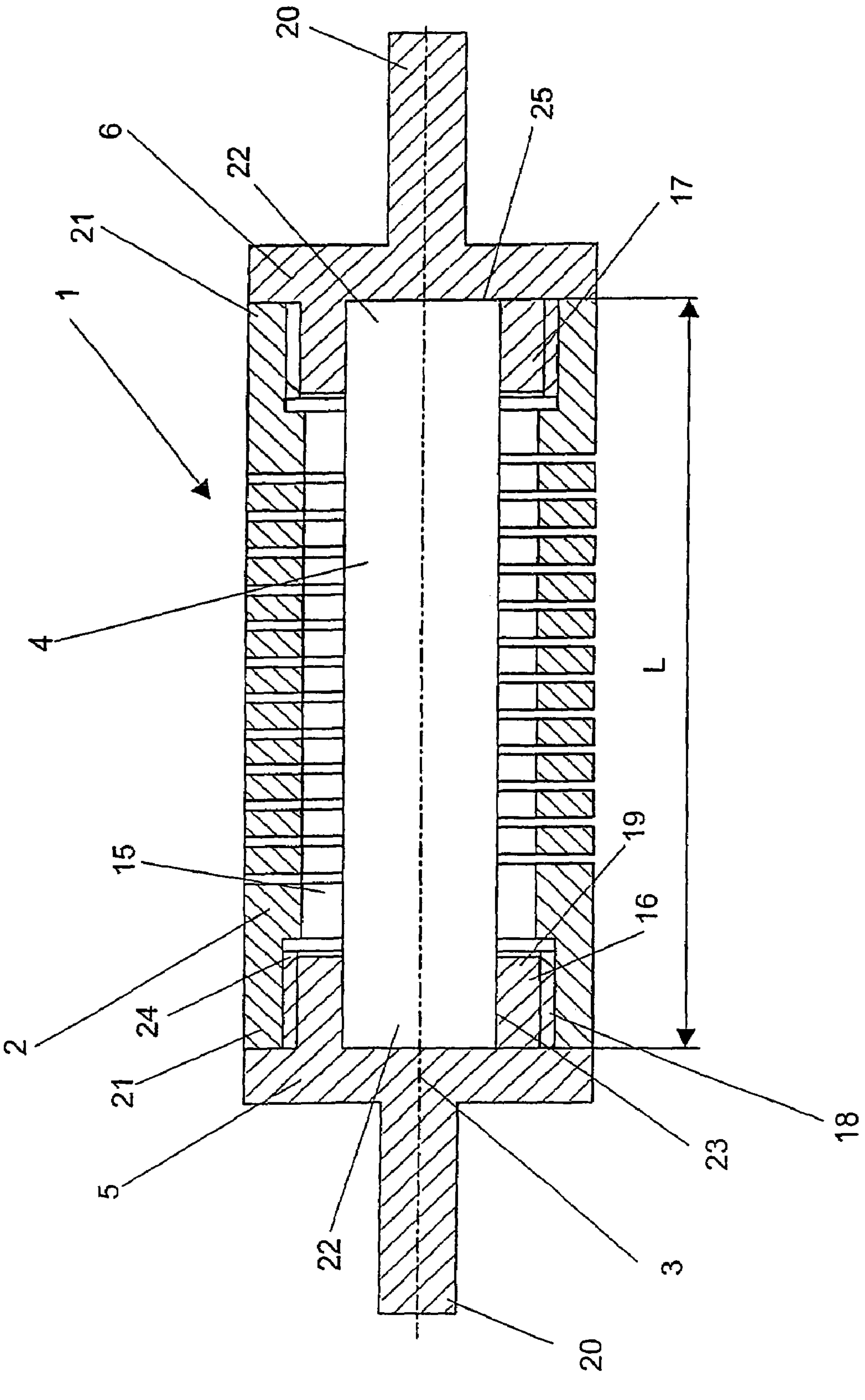
FIG. 1 is a longitudinal section of one embodiment mode of the damping element of the invention.

FIG. 1 shows an embodiment mode of the damping element 1 of the invention having two spring elements 2, 4 concentrically mounted with the longitudinal axis 3. The first spring element 2 is designed as a helical spring with a central cavity 15, whereas the second spring element 4 is bar-shaped and configured in said cavity 15. The end-side connectors 5, 6 also are mounted coaxially with the longitudinal axis 3 and each is fitted with a threaded segment 16, 17 with an outer thread 18, said segments being coaxial with the longitudinal axis 3 and pointing toward the spring elements 2, 4. The first spring element 2 is fitted at its axial ends 21 with inner threads 24 in the cavity 15 which match the outer threads 18, as a result of which the threaded segments of the connectors 5, 6 can be screwed into the first spring element 2. Moreover each connector 5, 6 comprises an open recess 23 configured coaxially with the longitudinal axis 3 at the inner end 19 of said connector, as a result of which the bar-shaped second spring element 4 can be received at its axial ends 22 in said recesses 23. The connectors 5, 6 also are coaxially bar-shaped at their outer end 20. When the damping element 1 is assembled, the ends 22 of the second spring 4 rest against the end faces 25 of the recesses 23 orthogonal to the longitudinal axis 3, and as a result the connectors 5, 6 are a distance L between these end faces 25. This distance L as well as the length of the undeformed first spring element 2 are selected in such a way that when the threaded segments 16, 17 are screwed into the inner threads 24, the first spring element 2 is stretched by a desired length and as a result prestressing is imparted to the damping element 1.

The spring rate of the first spring element 2 and the spring rate of the second spring element 4 differ by least a factor of 2, preferably by at least a factor of 5, and in some embodiments by a factor of between 10 and 100. The spring rate of the second spring element 4 may be between 100 N/mm and 5,000 N/mm and is preferably between 200 N/mm and 2,000 N/mm.

Figure 2:
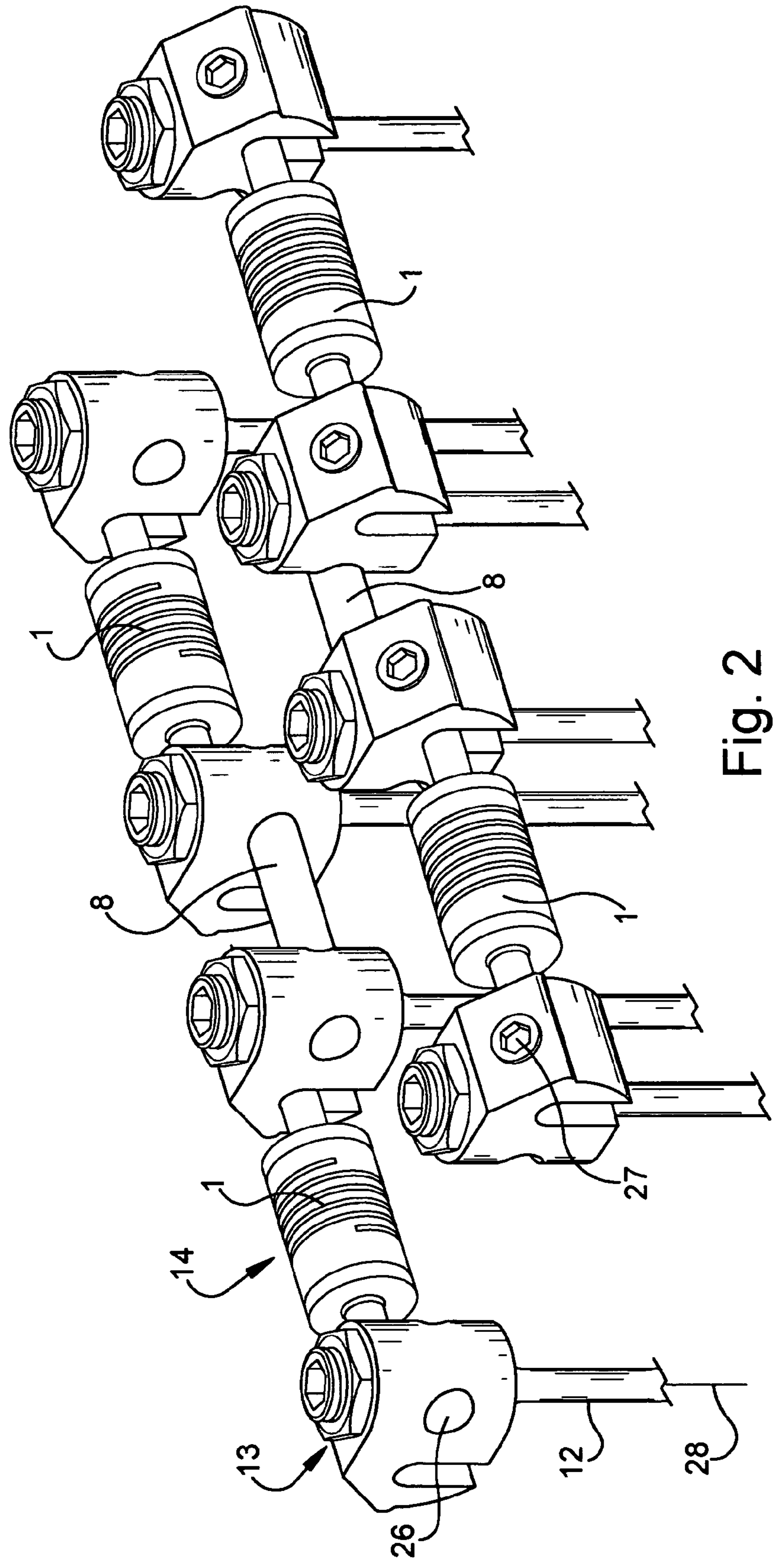
FIG. 2 is a view of an embodiment mode of the system of invention stabilizing adjacent vertebras.

FIG. 2 shows an embodiment mode of the system of the invention illustratively as a system stabilizing adjacent vertebras (omitted). Several pedicle screws or hooks 12 are affixed to the pedicles of vertebras to be connected so that their central axes 28 are configured transversely to the spinal column's longitudinal axis. The receiving means 13 at the pedicle screws or hooks 12 are mounted perpendicularly to the central axes 28 and are designed as ducts 26. The bar-shaped outer ends 20 of the connectors 5, 6 (FIG. 1) may be inserted into said ducts 26 and consequently the damping elements 1 are axially displaceable in the ducts 26 before being locked in place by screws 27 relative to the pedicle screws or hooks 12. The receiving means 13 at the pedicle screws or hooks 12 each comprise two parallel ducts 26 and allow locking for instance a bar-shaped affixation means 7 at a pedicle screw or hook 12 next to a damping element 1.

Figure 3:
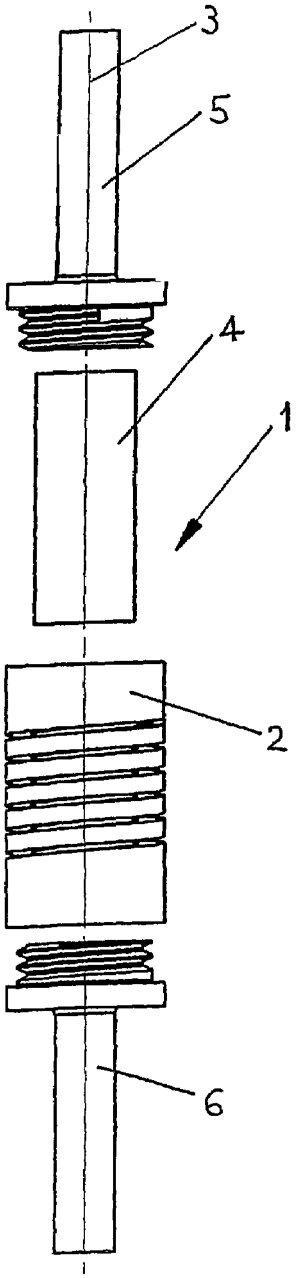
FIG. 3 is an exploded view of an embodiment mode of the damping element of the invention.

FIG. 3 shows an embodiment mode of the damping element 1 of the invention which comprises a first spring element 2 in the form of a helical spring, a bar-shaped second spring element 4 and two connectors 5, 6 configured coaxially with the longitudinal axis 3.

Figure 4:
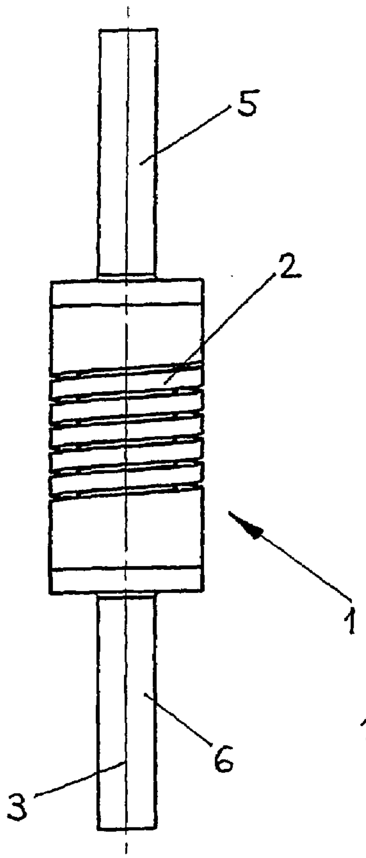
FIG. 4 is an elevation of an embodiment mode of the damping element of the invention.
Figure 5:
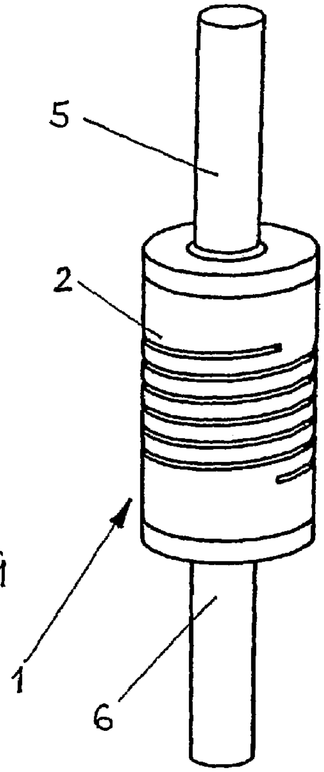
FIG. 5 is a perspective of an embodiment mode of the damping of the invention.

FIGS. 4 and 5 shown an embodiment mode of the damping element 1 of the invention comprising a first spring element 2 in the form of a helical spring and two connectors 5, 6 which are connected to the first spring element 2 and which are coaxial with the longitudinal axis 3.

Figure 6:
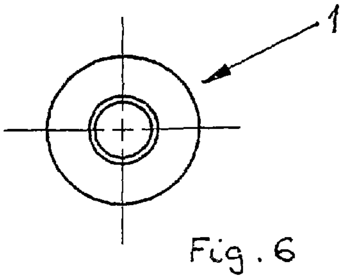
FIG. 6 is a topview of an embodiment mode of the damping element of the invention.

FIG. 6 is an embodiment mode of the damping element 1 of the invention which exhibits a circular cross-section orthogonally to the longitudinal axis 3. Other cross-sectional shapes, for instance oval or elliptical cross-sections, that might be advantageous in implanting the damping element 1 also are conceivable.

The invention claimed is:

1. A damping system comprising:

a damping element including:

two spring elements coaxial with or parallel to a longitudinal axis of the damping element, and two axially mounted end-side connectors linked to the spring elements such that at least one of the spring elements is connected to the connectors wherein:

the first spring element exhibits a spring rate F and has first and second ends positioned between the two end-side connectors, the second spring element exhibits a spring rate f and has first and second ends positioned between the two end-side connectors, the spring rates F and f are different from each other, one spring element comprises a spring coil;

the damping element is prestressed; and at least two bone fixation elements selected from the group comprising pedicle screws and pedicle hooks, wherein each of the bone fixation elements includes a duct for receiving the end-side connectors so that the damping element can span adjacent vertebra.

2. The damping system of claim 1, wherein the spring elements are configured concentrically with the longitudinal axis.

3. The damping system of claim 1, wherein at least one spring element is prestressed.

4. The damping system of claim 1, wherein the spring elements exhibit constant spring rates F, f.

5. The damping system of claim 1, wherein the damping unit's cross-section orthogonal to the longitudinal axis is reniform.

6. The damping system of claim 1, wherein one spring element is a compression spring.

7. The damping system of claim 6, wherein the spring element in the form of a compression spring is made of a polymer.

8. The damping system of claim 1, wherein one spring element is bar shaped.

9. The damping system of claim 1, wherein the second spring element is integral with one of the connectors.

10. The damping system of claim 1, wherein the second spring element is configured inside the first spring element.

11. The damping system of claim 1, wherein the two spring rates F, f differ at least by the factor 2.

12. The damping system of claim 11, wherein the two spring rates F, f differ by a factor of between 10 and 100.

13. The damping system of claim 1, wherein the spring rate f of the second spring element is between 100 N/mm and 5,000 N/mm.

14. The damping system of claim 13, wherein the spring rate f of the second spring element is between 200 N/mm and 2,000 N/mm.

15. The damping system of claim 1, wherein each end-side connector has a recess, and each end of the second spring element is shaped to fit within a respective recess.

16. The damping system of claim 1, wherein each end-side connector has a longitudinal bar-shaped extension at its outer end.

17. The damping system of claim 1, wherein the first spring element comprises a helical spring with a central cavity and the second spring element is shaped and configured to be positioned in the cavity.

18. A system stabilizing adjacent vertebras, comprising:

a damping element comprising:

two spring elements coaxial with or parallel to a longitudinal axis of the damping element, and two axially mounted end-side connectors linked to the spring elements such that at least one of the spring elements is connected to the connectors wherein:

the first spring element exhibits a spring rate F and has first and second ends positioned between the two end-side connectors, the second spring element exhibits a spring rate f and has first and second ends positioned between the two end-side connectors, the spring rates F and fare different from each other, one spring element comprises a spring coil; and the damping element is prestressed;

N pedicle screws or pedicle hooks, where N≧3, and at least one pedicle screw or one pedicle hook comprising receiving ducts simultaneously allowing receipt of two parallel longitudinal members, wherein the damping element is used for affixation between the at least one pedicle screw or pedicle hook and an adjacent pedicle screw or pedicle hook.

19. A damping element comprising:

two axially mounted end-side connectors, each having outer threads and a recess coaxial with a longitudinal axis of the damping element; and a first spring element coaxial with or parallel to the longitudinal axis, the first spring element having first and second ends each having inner threads that screw into the outer threads of a respective end-side connector, the first spring element comprising a helical spring with a central cavity; and a second spring element coaxial with or parallel to the longitudinal axis, the second spring element having first and second ends each shaped to fit within the recess of a respective end-side connector, the second spring element shaped and configured to be positioned in the central cavity of the first spring element; wherein:

the length of the second spring element causes the first spring element to be stretched beyond the first spring element's undeformed length when the end-side connectors are screwed into the first spring element.

20. A damping element comprising:

two spring elements coaxial with or parallel to a longitudinal axis of the damping element, and two axially mounted end-side connectors linked to the spring elements such that at least one of the spring elements is connected to the connectors wherein:

the first spring element exhibits a spring rate F and has first and second ends positioned between the two end-side connectors, the second spring element exhibits a spring rate f and has first and second ends positioned between the two end-side connectors, the spring rates F and f are different from each other, one spring element comprises a spring coil; and the damping element is prestressed, wherein each end-side connector has outer threads and each end of the first spring element has matching inner threads such that the connectors can be screwed into the first spring element.

21. A damping system comprising:

at least two bone fixation elements selected from the group comprising pedicle screws and pedicle hooks, wherein each of the bone fixation elements includes a channel; and a damping element having a longitudinal axis, the damping element comprising:

a pair of end-connectors, each end-connector having an inner end and an outer end wherein the outer ends are sized and configured to be received within the channels formed in the bone fixation elements; and first and second spring elements, the first spring element having a spring rate F, a first end, a second end and a central cavity, the second spring element having a spring rate f, a first end and a second end, the spring rates F and fare different from each other; and wherein the second spring element is sized and configured to be received within the central cavity of the first spring element and the first and second ends of the first and second spring elements are operatively connected to the inner ends of the end-connectors so that the first and second spring elements are positioned between the two end-connectors; and wherein the damping element is prestessed.

22. The damping system of claim 21, wherein the first spring element is a helical spring.

23. The damping system of claim 21, wherein the second spring element is bar-shaped.

24. The damping system of claim 21, wherein each of the inner ends of the end-connectors includes a threaded segment for threadably receiving threads formed on the first spring element.

25. The damping system of claim 21, wherein each of the inner ends of the end-connectors includes a recess for receiving the second spring element.

26. The damping system of claim 21, wherein the second spring element has a length L, the length L of the second spring element causes the first spring element to be stretched beyond the first spring element's undeformed length when the end-connectors are operatively connected to the first spring element.

27. The damping system of claim 21, wherein the second spring element is made from a polymer.

28. The damping system of claim 21, wherein the second spring element is made from a polycarbonate urethane.

* * * * *

UNITED STATES PATENT AND TRADEMARK OFFICE

CERTIFICATE OF CORRECTION

PATENT NO. : 7,329,258 B2
APPLICATION NO. : 10/497875
DATED : February 12, 2008
INVENTOR(S) : Armin Studer It is certified that error appears in the above-identified patent and that said Letters Patent is hereby corrected as shown below:

Column 6, line 7 reads -- the spring rates F and fare different from each other, -- should read -- the spring rates F and f are different from each other, --.

Column 7, line 5 reads -- the spring rates F and fare different from each other; -- should read -- the spring rates F and f are different from each other; --

Column 7, line 14 reads -- the damping element is prestessed -- should read -- the damping element is prestressed. --

Signed and Sealed this

Seventeenth Day of March, 2009

JOHN DOLL
*Acting Director of the United States Patent and Trademark Office*